(12) United States Patent
Sentmanat

(10) Patent No.: US 6,691,569 B1
(45) Date of Patent: Feb. 17, 2004

(54) DUAL WINDUP DRUM EXTENSIONAL RHEOMETER

(75) Inventor: Martin Lamar Sentmanat, Akron, OH (US)

(73) Assignee: The Goodyear Tire & Rubber Company, Akron, OH (US)

(*) Notice: Subject to any disclaimer, the term of this patent is extended or adjusted under 35 U.S.C. 154(b) by 33 days.

(21) Appl. No.: 10/208,954

(22) Filed: Jul. 31, 2002

(51) Int. Cl.⁷ ................................................. G01F 3/04
(52) U.S. Cl. ....................................................... 73/261
(58) Field of Search ........................... 73/159, 160, 261; 242/125; 318/7, 12

(56) References Cited

U.S. PATENT DOCUMENTS

| | | | |
|---|---|---|---|
| 4,789,107 A | * 12/1988 | Hauser et al. | 242/413.7 |
| 4,945,293 A | * 7/1990 | Wittkopf et al. | 318/7 |
| 5,092,168 A | * 3/1992 | Baker | 73/159 |
| 5,201,424 A | * 4/1993 | Hain | 209/534 |

* cited by examiner

Primary Examiner—Edward Lefkowitz
Assistant Examiner—Jewel V. Thompson
(74) Attorney, Agent, or Firm—Howard M. Cohn

(57) ABSTRACT

An extensional rheometer comprises a rotatable primary wind up drum and one or more secondary rotatable windup drums wherein a sample is attached to the primary windup drum and each secondary windup drum. Counter rotation of the primary windup drum and each secondary drum causes each affixed sample to stretch until rupture. The load response on each primary and secondary windup drum set caused by a stretching sample is measured with a load sensing device. Environmental control may be provided for testing samples under different conditions.

16 Claims, 7 Drawing Sheets

DUAL WINDUP DRUM EXTENSIONAL RHEOMETER

RELATED APPLICATIONS

This application relates to U.S. application Ser. No. 09/849,934 entitled Dual Windup Extensional Rheometer by Martin Sentmanat and having a common assignee with the present invention.

TECHNICAL FIELD

The invention relates to a rheometer or rheometer attachment which is used to measure the viscosity and stress relaxation of polymers, elastomers, and rubber compounds in simple extension. More specifically, the present invention relates to the utilization of a dual windup drum method to characterize the extensional flow behavior of one or more material samples simultaneously.

BACKGROUND ART

Joachim Meissner, in the review article "Polymer Melt Elongation-Methods, Results, and Recent Developments" in Polymer Engineering and Science, April 1987, Vol. 27, No. 8, pp. 537–546 describes different extensional rheometers that have been developed in the prior art. Meissner is also the author of several patents on the subject including U.S. Pat. No. 3,640,127, dated Feb. 8, 1972, German 2,138,504, dated Aug. 2. 1971, German 2,243,816, dated Sep. 7, 1972 and U.K. 1,287,367.

Extensional rheometer designs by Cogswell, Vinogradov, and later Muinstedt had in common that one end of the polymer fiber or filament that was used for testing was fixed to a load cell/indicator, while the other end was stretched by mechanical means to a finite maximum elongation. Accordingly, these rheometers operated with a non-uniform extensional rate throughout the sample particularly near the clamped ends of the fiber. Meissner overcame these difficulties with his dual rotary clamp design in which rotary clamps stretched the fiber at either end over a fixed gauged length. See, for example, "Rotary Clamp in Uniaxial and Biaxial Extensional Rheometry of Polymer Melts" by J Meissner, et al., Journal of Rheology, Vol. 25, pp. 1–28 (1981) and "Development of a Universal Extensional Rheometer for the Uniaxial Extension of Polymer Melts", by J Meissner, Transactions of the Society of Rheology, Vol. 16, No. 3, pp. 405–420 (1972). In a further development of this type of rheometer, in order to improve the transfer of the circumferential speed of the clamps to the local speed of the sample at the location of clamping (strain rate lag), two rotary clamps in the prior art devices were replaced by Meissner and Hostettler as illustrated in "A New Elongational Rheometer for Polymer Melts and other Highly Viscoelastic Liquids", Rheological Acta, Vol. 33, pp. 1–21 (1994) with matched/grooved, metal conveyor belts. With this design, however, a measurement was limited to a single rotation of the clamps corresponding to a Hencky strain of seven, and the maximum extensional rate was limited to 1/s (a reciprocal second). The extensional viscosity was determined from the force required to deform the fiber, which was measured by the deflection of leaf springs supporting one set of rotating clamps. However, as has been reported in the literature by Erik Wassler in "Determination of true extensional viscosities with a Meissner-type rheometer (RME)", Proceedings of the 15$^{th}$ Annual Meeting of the Polymer Processing Society, Paper 200 (1999), there can be large deviations between the nominal and the true extensional strain with this type of extensional rheometer due to sample slippage between the rotating clamps.

Other techniques used to measure extensional viscosity involved winding one end of a fiber around a drum and measuring the resultant stretching force at the other fixed end of the fiber, as described in an article by R. W. Connelly, et al., "Local Stretch History of a Fixed-End-Constant-Length-Polymer-Melt Stretching Experiment," J. Rheol., Vol. 23, pp. 651–662 (1979). Like the earlier designs, this method imparts a non-uniform extensional deformation to the free gauge length of the stretched fiber, particularly at the fixed end of the fiber that can lead to a false material rupture condition during extension.

There remains a need to measure extensional viscosity and stress relaxation of one or multiple polymers, elastomers, and rubber compounds in uniaxial extension simultaneously. Steps to overcome the latter limitations were disclosed in PCT Publication No. WO00/28321 entitled Dual Windup Extensional Rheometer by Martin Sentmanat and having a common assignee with the present invention. Setting out to improve upon the shortcomings of sample slippage and the non-uniform deformations encountered with other extensional rheometer designs, Sentmanat in PCT Publication No. WO00/28321 described an apparatus in which both ends of a material sample are wound around a set of mechanically coupled counter-rotating drums housed in a torque armature. Upon stretching the sample, the extensional resistance of the material sample hinders drum rotation, and the extensional flow behavior of the sample material can be characterized by monitoring the torque on the torque armature required to rotate the windup drums at a fixed rate of rotation. Like the earlier designs, the rheometer described in WO00/28321 is only capable of assessing a single sample material at a time. In addition, because the master and slave drums of the device described in WO00/28321 are both mounted on bearings within the torque armature, friction from the bearings due to the rotation of the master and slave drums contribute to the measured signal during an experiment.

There remains a need to provide a rheometer that can measure a plurality of samples at one time and measures the samples with torque signals that do not include friction from bearings supporting the drums.

SUMMARY OF THE INVENTION

According to an embodiment of the present invention, there is disclosed an extensional rheometer apparatus for measuring the extensional flow response of samples of material, such as a low modulus solid sample. The rheometer comprises a primary windup drum mounted to a power drive device for rotating the primary windup drum; a secondary windup drum rotatably mounted in proximity to the primary windup drum; means interconnecting the primary windup drum to the secondary windup drum whereby rotation of the primary windup drum by the power drive device causes the rotation of the secondary windup drum; and a load sensing device for measuring the response of the extensional flow of a low modulus solid sample secured to the primary windup drum and the secondary windup drum.

Further, according to the present invention, the primary and secondary windup drums are preferably in substantially parallel alignment. Further, the means for interconnecting the primary and secondary windup drums are first and second gears individually attached to the primary and secondary windup drums and intermeshed such that the primary and secondary windup drums are counter rotating and cause the primary and secondary windup drums to rotate at the same speed.

Also, according to the present invention, the load sensing device is attached to the secondary windup drum for supporting the secondary windup drum. In an alternative embodiment, the load sensing means is attached to the primary windup drum driving means.

According to another embodiment of the present invention, an extensional rheometer apparatus for measuring the extensional flow response of samples of material, such as a plurality of low modulus solid samples, comprises a primary windup drum mounted to a power drive device for rotating the primary windup drum; a plurality of secondary windup drums rotatably mounted in proximity to the primary windup drum; means interconnecting the primary windup drum to the plurality of secondary windup drums whereby rotation of the primary windup drum by the power drive device causes the rotation of the secondary windup drums; and a load sensing device attached to each of the secondary windup drums for supporting each of the secondary windup drums and measuring the response to the extensional flow of low modulus solid samples secured to the primary windup drum and each of the plurality of secondary windup drums.

Further, according to the latter embodiment of the present invention, the primary and plurality of secondary windup drums are in substantially parallel alignment. Also, the means for interconnecting the primary and plurality of secondary windup drums are first and second gears individually attached to the primary and plurality of secondary windup drums and intermeshed such that the primary and plurality of secondary windup drums are counter rotating and rotate at the same speed.

According to another embodiment of the present invention, an extensional rheometer apparatus for measuring the extensional flow response of samples of material, such as a low modulus solid sample, comprises a primary windup drum mounted to a primary power drive device for rotating the primary windup drum; a secondary windup drum rotatably mounted to a secondary power drive device for rotating the secondary windup drum in proximity to the primary windup drum; and a load sensing device attached to the secondary power drive device for supporting the secondary windup drum and measuring the extensional flow response of a low modulus solid sample secured to the primary windup drum and the secondary windup drum. The load sensing device is secured at one end to a support member and at the other end to the secondary power drive device.

According to yet another embodiment of the present invention, an extensional rheometer apparatus for measuring the extensional flow response of samples of material, such as a of low modulus solid samples comprises a primary windup drum mounted to a primary power drive device for rotating the primary windup drum; a plurality of secondary windup drums rotatably mounted to a plurality of secondary power drive devices for individually rotating the secondary windup drums in proximity to the primary windup drum; and a plurality of load sensing devices, each attached to one of the plurality of secondary power drive devices for supporting the plurality of secondary windup drums and measuring the extensional flow response of low modulus solid samples secured to the primary windup drum and each of the secondary windup drums. Each of the plurality of load sensing devices are secured at one end to a support member and at the other end to one of the plurality of secondary power drive devices.

According to yet another embodiment of the present invention, a method for measuring the extensional flow response of a material, such as a low modulus solid sample comprising the steps of: rotating a primary windup drum with a power drive device; rotating a secondary windup drum in proximity to the primary windup drum; and supporting the secondary windup drum and measuring the extensional flow response of a low modulus solid sample secured to the primary windup drum and the secondary windup drum with a load sensing device. The method includes the steps of rotating a plurality of secondary windup drums in proximity to the primary windup drum; and supporting the plurality of secondary windup drums and measuring the extensional flow response of a plurality of low modulus solid samples secured to the primary windup drum and the plurality of secondary windup drums with a plurality of load sensing devices each attached to the plurality of secondary windup drums.

DETAILED DESCRIPTION OF THE INVENTION

Figure 1:
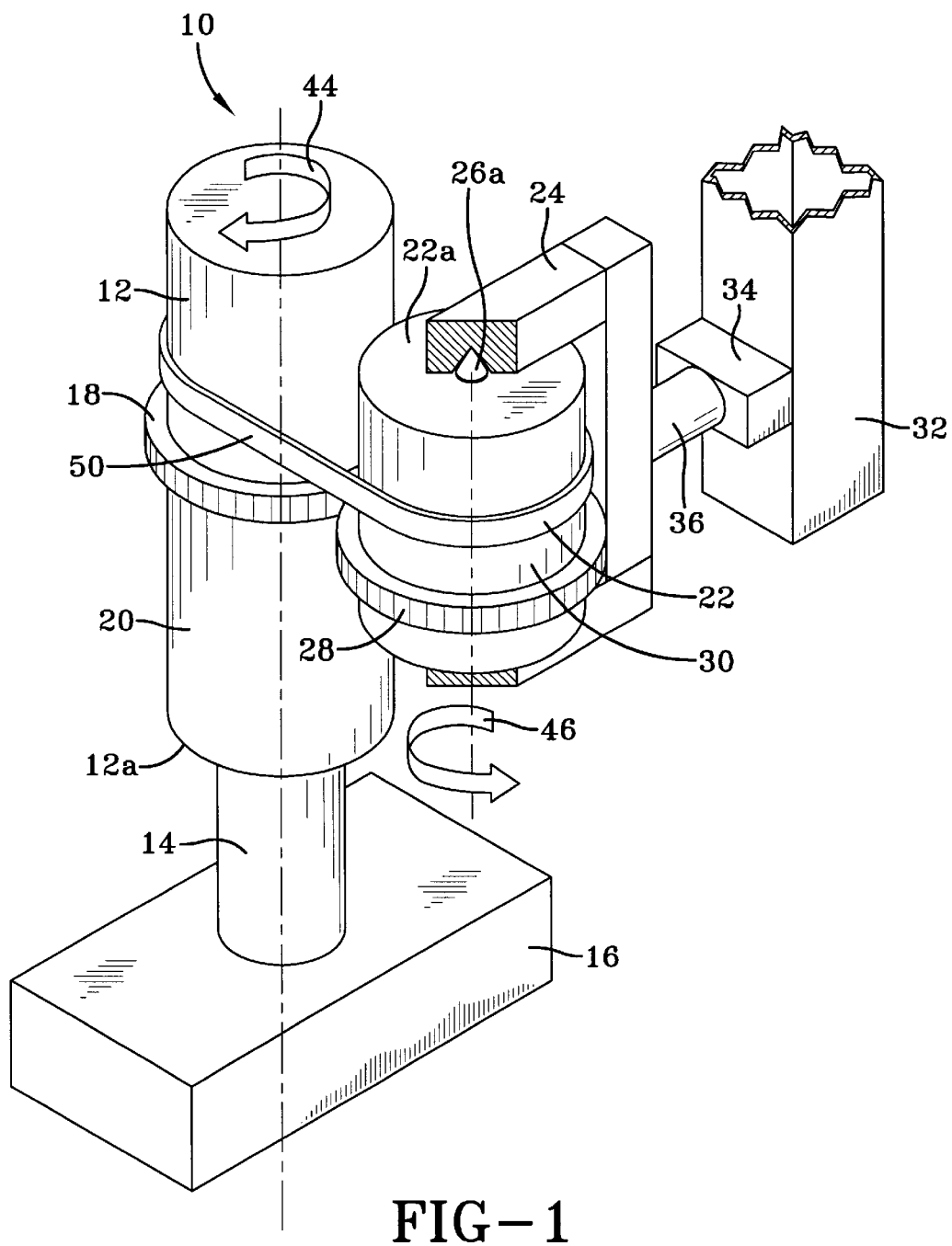
FIG. 1 illustrates a perspective view of a first embodiment of the rheometer apparatus of the present invention including a primary windup drum in parallel relation to a secondary windup drum illustrated as mounted in a cutaway section of a mounting bracket.
Figure 2:
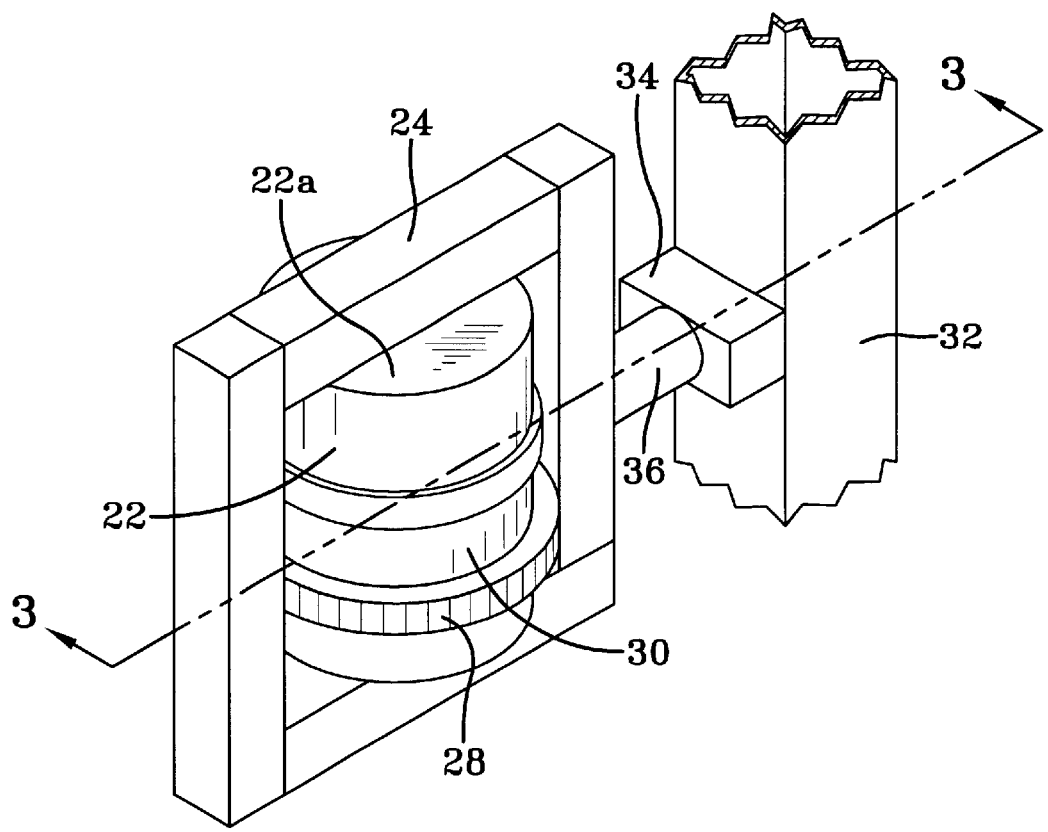
FIG. 2 illustrates a perspective view of the secondary windup drum shown in FIG. 1 secured in a mounting bracket attached to a vertical support frame via a load sensing device.
Figure 3:
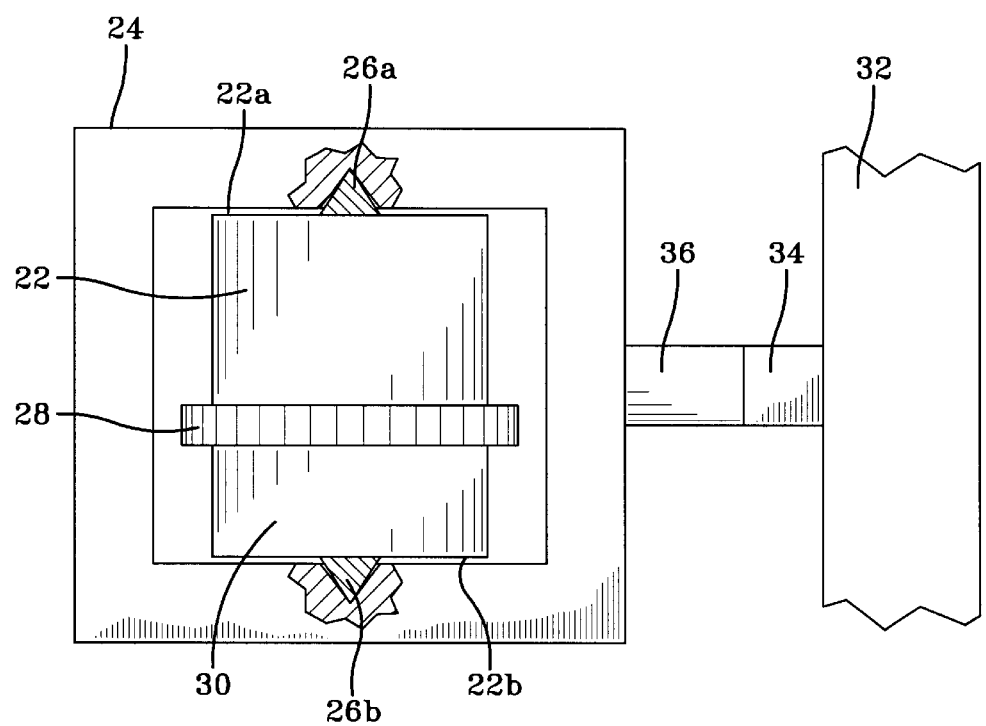
FIG. 3 is a cross sectional view through line 3—3 of FIG. 2 showing the secondary windup drum in a mounting bracket attached to a vertical support frame via a load sensing device.

With reference now to FIGS. 1–3, there is illustrated a first embodiment of a rheometer apparatus 10. The rheometer apparatus 10 has a primary windup drum 12 connected at one end 12a to one end of a primary drive shaft 14. The opposite end of the drive shaft 14 is mounted to a drive motor 16, such as a conventional electrically powered motor. The primary windup drum 12 has a primary drive gear 18, typically a fine toothed, spur gear, on the circumferential outward surface 20 of the drum.

In the illustrated embodiment, primary windup drum 12 is illustrated as being in direct alignment with drive shaft 14. Those skilled in the art will recognize that this alignment is not necessary for operation of the apparatus, but is preferred to make construction easier and simplify the calculations of torque.

A secondary windup drum 22 is disposed in parallel relation to the primary windup drum 12. The secondary windup drum 22 is supported by a support frame 24 as seen in FIGS. 1, 2 and 3. The outward ends 22a, 22b of the secondary drum 22 can include bearings 26a and 26b respectively, to provide low frictional rotation between the secondary drum and the support frame 24. While the support frame 24 is illustrated with a square configuration to completely enclose the secondary drum 22, it is within the terms of the present invention to form the support frame with other shapes as long as they can carry out the function as described hereinafter. The secondary winding drum 22 has a secondary drive gear 28, typically a fine toothed, spur gear, disposed about the circumferential surface 30 of the secondary drum. The primary and secondary windup drums 12 and 22 are disposed so that the primary and secondary gears 18 and 28 intermesh so that the turning of the primary gear causes the turning of the secondary gear.

As shown in FIGS. 1–3, the support frame 24 is affixed to a load sensing device 34 such as a piezoelectric load cell or a strain-gage force transducer via a support member 36. In turn the load sensing device 34 is securely attached to a support member 32.

All of the windup drums referenced herein are typically but not limited to axisymmetric cylinders of the same diameter. In the case of non-axisymmetric cylinders, a non-constant rate of drum rotation would need to be employed in order to maintain a constant rate of extensional deformation with regards to a true strain deformation, also referred to as a Hencky strain.

Each of the windup drums 12 and 22 have associated therewith a securing means (not shown), such as a sample cradling pin or other clamping mechanism, as shown and described in WO00/28321, which is incorporated in its entirety by reference herein, to attach a filament to the drums as required to carry out the measurements desired. It can be appreciated in viewing FIG. 1 that the drive motor 16 turns the drive shaft 14 which in turn rotates the primary winding drum 12 and its attached primary drive gear 18 in a clockwise direction as indicated by arrow 44. Gear 18, in turn, turns gear 28 in a counter-clockwise direction as indicated by arrow 46, which causes rotation of the secondary windup drum 22. The rotation of the primary and secondary drums 12 and 22 stretches the sample material 50 of a polymer, elastomer, or compound. The resistance provided by the stretched sample 50 to the turning of the secondary windup drum 22 imparts a force on the support frame 24 via the bearings 26a and 26b, which is then imparted through the support member 36 into the load sensing device 34, the latter being fixedly attached to support member 32. The force imparted into the load sensing device 34 tends to move the load sensing device in a direction that follows the rotation of the primary windup drum 12. The tendency of the support structure 24 to turn in the motion of the primary drum rotation (even though it cannot turn because it is secured to support member 32) creates a load on the support member 36 and load sensing device 34 that can be measured. The apparatus in each of the embodiments of the present invention is designed so that support member 36 does not actually move, but a load on support member 36 activates the load sensing device which, through a closed feedback loop in the apparatus, develops a current which tends to counteract the load imposed on support member 36 by the secondary windup drum 22 in the support frame 24, and the current required to counteract this load is measured, thereby measuring the load generated. Such force rebalance systems are well known to those skilled in the art. Other techniques of measuring loads are known to those skilled in the art, and such other techniques can be used with the apparatus of the invention.

In the operation of the apparatus 10 of the first embodiment of the invention, the ends of a prepared sample 50 are first secured to the windup drums 12 and 22 by a securing means. In the case of constant radius windup drums, constant rotation of the windup drums 12 and 22 imparts a constant, uniform extensional deformation rate to the unsupported length of the prepared sample 50. The zone of deformation, or stretch, for the material sample is defined by the tangent line spanning the windup drum pair. The extensional deformation of the material sample offers a resistance to elongation (related to the extensional flow properties of the material) which in turn offers a resistant load on the secondary drum that is resolved with the associated sensing means. Thus by measuring the resulting force that is perpendicular to the primary axis of deformation on the secondary drum 22, the extensional stress, or viscosity, of the associated material being deformed can be determined for a given rate of extensional deformation.

In the special case for which the drive motor 16 has incorporated therein a means of resolving the resistant torque on the motor for a given rate of rotation, the resultant torque imparted on the primary windup drum 12 may be resolved to determine the resistance to elongation of the sample. In any case, the extensional deformation of the stretched sample 50 offers a resistance to deformation that is related to the extensional viscosity of the sample, which in turn offers a resistance to the primary drum rotation in the form of a resulting torque on the drive motor 16. By measuring the resultant torque transmitted to the drive motor 16, the extensional viscosity of the prepared sample 50 may be calculated for a given rate of extensional deformation.

While not shown, it is within the scope of the present invention to place the apparatus 10 within an environmental chamber, that can be used to heat or cool the sample as desired so that extensional flow properties of a material may be calculated as a function of extensional deformation rate and temperature. The environmental chamber is designed to measure rheology of samples from −70 degrees Centigrade (C) to 300 degrees Centigrade. Measurements at lower temperatures are designed to measure extensional rheology as it relates to Tg (glass transition) of the sample and the extensional flow of the materials at higher temperatures is related to the melts/viscosity of the sample. The environmental chamber can be in the form of an evan or an oil bath or any other means known to those skilled in the art for controlling the physical state of a sample.

Figure 4:
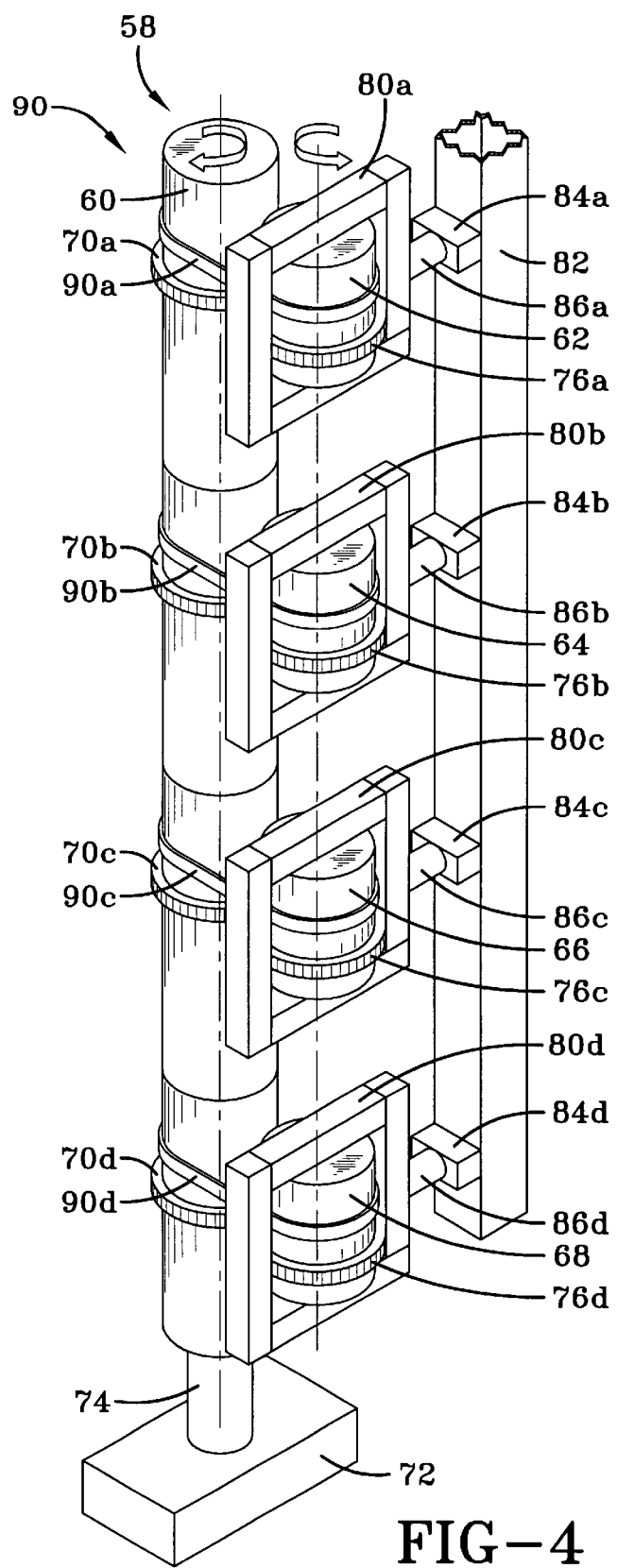
FIG. 4 illustrates a perspective view of an alternative embodiment of the rheometer apparatus of the invention of FIG. 1 illustrating a primary windup drum in parallel relation to a plurality of secondary windup drums.

Referring to FIG. 4, there is illustrated a second alternative embodiment of the present invention wherein rheometer system 58 is provided with a single primary drive shaft 60 that is designed to operate a plurality of secondary winding drums 62, 64, 66, 68 (62–68). The primary drive shaft 60 includes a plurality of spaced primary drive gears 70a, 70b, 70c, 70d. As in the first embodiment shown in FIGS. 1–3, the primary drum 60 is operated by a drive motor 72, which can be operationally connected to the primary drum 60 by any means such as a drive shaft 74. Each of the secondary drums 62–68 have secondary gears 76a, 76b, 76c, 76d, respectively, which mesh with the primary gears 70a–70d, respectively. As discussed with respect to the first embodiment, each of the secondary drums 62–68 is mounted within a support frame 80a, 80b, 80c, 80d (80a–80d), which are secured to a support member 82 via load sensing devices 84a, 84b, 84c, 84d (84a–84d), respectively, via support members 86a, 86b, 86c, 86d (86a–86d), respectively.

In operation of the second embodiment, as shown in FIG. 4, a plurality of prepared samples 90a, 90b, 90c, 90d (referred collectively as 90 herein), are secured to the primary and secondary windup drums 60 and 62–68, respectively. While four secondary drums 62–68 are illustrated, it is within the terms of the invention to have more or fewer secondary drums as desired. Further, while it is illustrated that all of the primary and secondary drums 60 and 62–68, respectively, are loaded with the prepared samples 90, it is also within the terms of the invention to operate the system 58 with any number of the secondary windup drums 62–68 as desired. In the case where constant radius windup drums are used, the constant rotation of the primary and secondary windup drums 60 and 62–68 imparts a constant, uniform extensional deformation rate to the unsupported pre-gauge length of the prepared samples 60. The extensional deformation of the stretched samples 60 offers a resistance to deformation which is related to the extensional viscosity of the samples, which in turn offers a resistance to the rotation of the secondary drums 62–68 in the form of a resulting load on the load sensing devices 84a–84d. By measuring the resulting force on the load sensing devices 84a–84d, the extensional viscosity of each of the material samples 90a–90d respectively, can be calculated for a given rate of extensional deformation and temperature. Again, as with the first embodiment, it is within the scope of the present invention to place the system 58 within an environmental chamber (not shown), which can be used to heat or cool the sample as desired.

Figure 5:
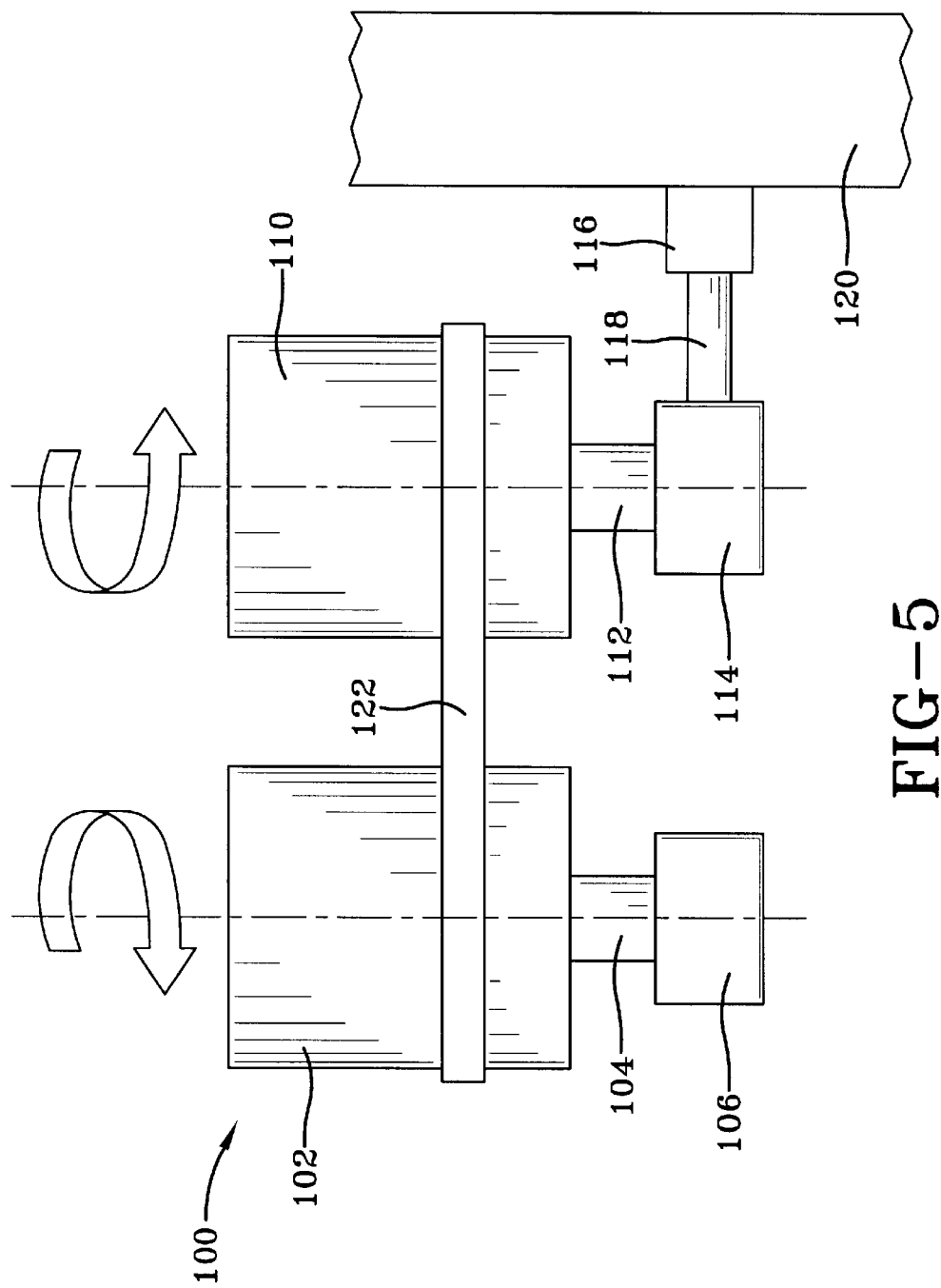
FIG. 5 illustrates a side view of a second embodiment of the present invention including a primary rotating drum with an independent power supply in parallel relation to a secondary rotating drum with an independent power supply.

Referring to FIG. 5, there is illustrated a third embodiment of the invention. The rheometer apparatus 100, as shown in FIG. 5, includes a primary windup drum 102 connected at one end to a drive shaft 104. The drive shaft 104 itself is mounted to a drive motor 106, such as a conventional, electrically powered motor of the type described with regards to the first embodiment of the invention.

A secondary windup drum 110 is disposed in parallel to the primary windup drum 102. The secondary windup drum 110 is supported on a drive shaft 112, which is attached at an opposite end to a drive motor 114 of a desired type, such as electrically powered motor 106. The motor 114 is affixed to a load sensing device 116 (compare load sensing device 34), via a support member 118. The load sensing device 116 is secured to a support member 120. Each of the windup drums 102 and 110 have associated therewith securing means such as disclosed in WO00/28321, to attach a material sample 122 of the type sample described herein before as required to carry out the measurements desired. Similar to the first embodiment, the motors 106 and 114 are operated to turn the drive shafts, 104 and 112, respectively, and the primary and secondary winding drums 102, 110, respectively, in opposite directions. For example, the primary drum 102 can turn in a clockwise direction while the secondary drum 110 can turn in a counter-clockwise direction as shown by the arrows. The rotation of the primary and secondary drums 102 and 110, respectively, causes the sample 122 of a polymer, elastomer or compound to stretch. The resistance provided by the stretched sample 122 to the turning of the secondary windup drum 110 imparts a force on the motor 114, which is then imparted through the support member 118 into the load sensing device 116, the latter being fixedly attached to support member 120. The load on motor 114 that is transmitted through support member 118 may be resolved by load sensing device 116 with respect to support member 120 as a force tending to bring secondary drum 110 towards primary drum 102 or as a resistant torque tending to hinder the rotation of secondary drum 110. This force or torque response can be measured from the load sensing device 116 by conventional means.

In operation of the rheometer apparatus 100 of the third embodiment of the invention, the ends of the prepared sample 122 are secured to the primary and secondary drums 102 and 110. Constant rotation of constant radius windup drums 102, 110 imparts a constant, uniform extensional deformation rate to the unsupported pre-gauge length of the prepared sample 122. The extensional deformation of the stretched sample 122 offers a resistance to deformation which is related to the extensional viscosity of the sample, which in turns offers a resistance to the drum 110 rotation in the form of a resulting load on the load sensing device 116. By measuring the resulting load on the load sensing device 116, the extensional viscosity of the material sample can be calculated for a given extensional deformation rate and temperature.

Since the windup drums 102, 110 in the device 100 described in the embodiment of FIG. 5 of the present invention can be mounted directly on the driving means 106, 114, respectively, the use of bearings for the windup drums is not required and thus the frictional contribution from the drum rotation is obviated. Furthermore, since the primary and secondary drums 102, 110, respectively have unique drive systems, the frictional contribution from any mechanical drive coupling (i.e. intermeshing gears) on the measured signal may also be obviated.

Material sample strips/fibers 122 are prepared and secured against a set of mated primary and secondary windup drums that comprise an extensional rheometer system 100. The rheometer may be comprised of either a single cell or multiple cells in which multiple samples may be characterized simultaneously. The drive means for the primary drum may be common to each to the multiple cells whereas each secondary drum and drive means are unique to a cell. The secondary drum of each cell rotates counter to the rotation of the primary drum and has associated with it a sensing means for resolving the load on the secondary drum. Rotation of the primary and secondary windup drums imparts a uniform extensional deformation to the secured material sample associated with each rheometer cell. The zone of deformation, or stretch, for each material sample is defined by the tangent line spanning each windup drum pair. The extensional deformation of the material sample offers a resistance to elongation (related to the extensional flow properties of the material) which in turn offers a resistant load on the secondary drum that is resolved with the associated sensing means. Thus by measuring the resulting load on each secondary drum, the extensional stress, or viscosity, or each associated material being deformed can be determined for a given rate of extensional deformation. Each cell may be accommodated within an environmental chamber such that the extensional flow properties of materials may be characterized with respect to temperature.

Figure 6:
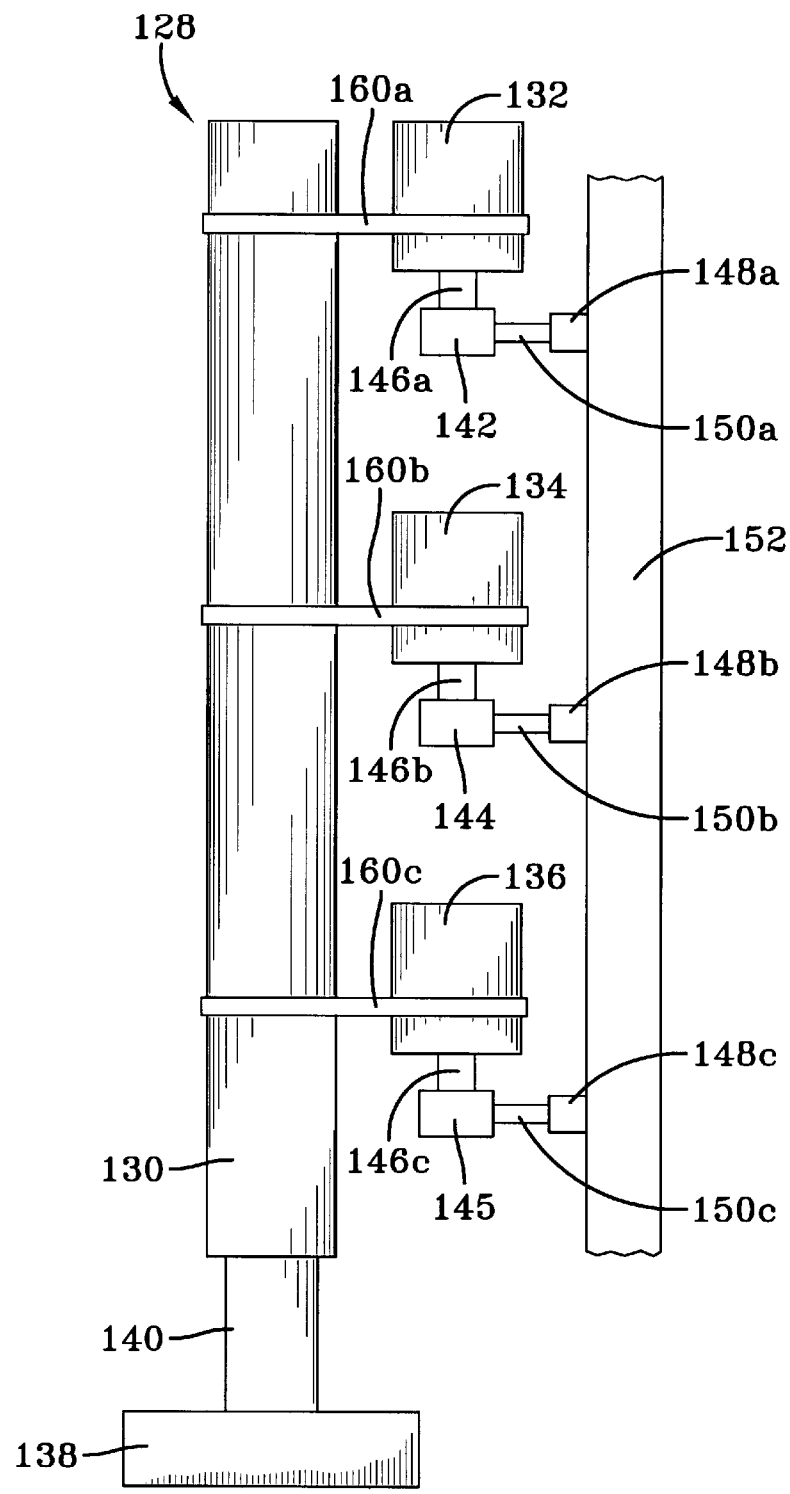
FIG. 6 illustrates a side view of a second embodiment of the present invention including a primary rotating drum with an independent power supply in parallel relation to a plurality of secondary rotating drums each with an independent power supply.

Referring to FIG. 6, there is shown an alternative embodiment of a rheometer system 128 incorporating the invention shown in FIG. 5. In the embodiment of FIG. 6, there is a single primary winding drum 130 designed to operate in conjunction with a plurality of secondary winding drums 132, 134, 136. As in the embodiment shown in FIG. 5, the primary winding drum 130 is operated by a drive motor 138 (compare 106) connected to the primary drum 130 by means such as a drive shaft 140. Each of the secondary winding drums 132, 134, 136 has a separate drive motor 142, 144, 146, respectively, (compare 114) adapted to rotate their respective secondary winding drum through a drive shaft 146a, 146b, 146c, respectively. As in the embodiment shown in FIG. 5, each of the drive motors 142, 144, 146, which act to support and turn the secondary winding drums 132, 134, 136, respectively, is secured to a load sensing device 148a, 148b, 148c (collectively known as 148), respectively, by a support member 150a, 150b, 150c, respectively. Each of the load sensing devices 148a, 148b, 148, (compare 116 in FIG. 5) and are secured to a support member 152. Each of the secondary winding drums 132, 134, 136 operate independently of each other so that any or all of the plurality of secondary winding drums can be used at the same time or at different times. As shown in FIG. 6, the ends of the prepared samples 160a, 160b, 160c are secured to the primary and secondary drums 130 and 132–136, respectively, by a securing means. As described in the embodiment shown in FIG. 5, the rotation of the primary and secondary drums 130 and 132–136, respectively, cause the sample of a polymer elastomer compound to stretch. The resistance provided by the stretched samples 160a, 160b, 160c to the turning of the secondary windup drums 132–136, respectively, imparts a force on the motors 142, 144, 145, which in turn is imparted through the support members 150a, 150b, 150c, respectively, into the load sensing devices 148a, 148b, 148c, respectively. The latter load sensing devices 148a, 148b, 148c are attached to the support member 152 so that the force imparted into each of the load sensing devices moves the load sensing device and creates a torque with respect to the support member 152. The torque can be measured from the load sensing devices 148a, 148b, 148c by conventional means. The primary motor 138 and the secondary motors 142, 144, 145 are operated to provide constant speed of rotation of the primary and secondary winding drums 130 and 132–136, respectively, to impart a constant, uniform extensional deformation rate to the unsupported pre-gauge length of the prepared samples 160a, 160b, 160c. The zone of deformation, or stretch, for each material sample is defined by the tangent line spanning each windup drum pair. The extensional deformation of the material sample offers a resistance to elongation (related to the extensional flow properties of the material) which in turn offers a resistant load on the secondary drum that is resolved with the associated load sensing device. Thus by measuring the resulting load that is parallel to the primary axis of deformation on each secondary drum, the extensional stress, or viscosity, or each associated material being deformed can be determined for a given rate of extensional deformation. The extensional deformation of the material samples 160a, 160b, 160c offers a resistance to deformation which is related to the extensional viscosity of the samples. This resistance, in turn, offers a resistance to the secondary drum rotation in the form of a resulting load on the load sensing devices 148a, 148b, 148c. By measuring the resulting loads on each of the load sensing devices 148a, 148b, 148c, the extensional viscosity of the material samples 160a, 160b, 160c can be calculated for a given extensional deformation rate and temperature.

While three secondary winding drums 132, 134, 136 are shown in FIG. 6, it is within the terms of the present invention to use any number of secondary winding drums as desired. Also, the rheometer system 128 shown in FIG. 6 can be placed in an environmental chamber, as described hereinbefore.

Since the primary windup drum 130 and the secondary windup drums 132, 134, 136 of the extensional rheometer device 128 described with respect to the embodiment of FIG. 6 of the present invention can be mounted directly on the driving means 138 and 142,144 and 145, respectively, the use of shaft bearings for the windup drums is not required and thus the frictional contribution from the drum rotation is obviated. Furthermore, since the primary and secondary drums 130 and 132,134,136, respectively, have unique drive systems, the frictional contribution from any mechanical drive coupling (i.e. intermeshing gears) on the measured signal may also be obviated.

Material sample strips/fibers 160a, 160b, 160c are prepared and secured against a set of mated primary and secondary windup drums 130 and 132,134,136, respectively, that comprise the extensional rheometer system 128. The rheometer system may be comprised of either a single set of drums, as shown in FIG. 5 or multiple drums, as shown in FIG. 6. In the latter embodiment, multiple samples may be characterized simultaneously.

The invention is further illustrated with reference to the following example.

EXAMPLE 1

The apparatus 10 shown in FIGS. 1–3 is used for illustrative purposes in this example.

Both ends of an uncured polymer filament 50 are secured by the sample securing clamps of the equal diameter, primary and secondary windup drums 12,22, respectively, of the extensional rheometer 10. A motor 16 rotating at a fixed rotational rate drives the primary windup drum 12 and a fine toothed, spur gear 18 on the same shaft 14. This spur gear 18 intermeshes with a similar spur gear 28 on the secondary windup drum 22.

Figure 7:
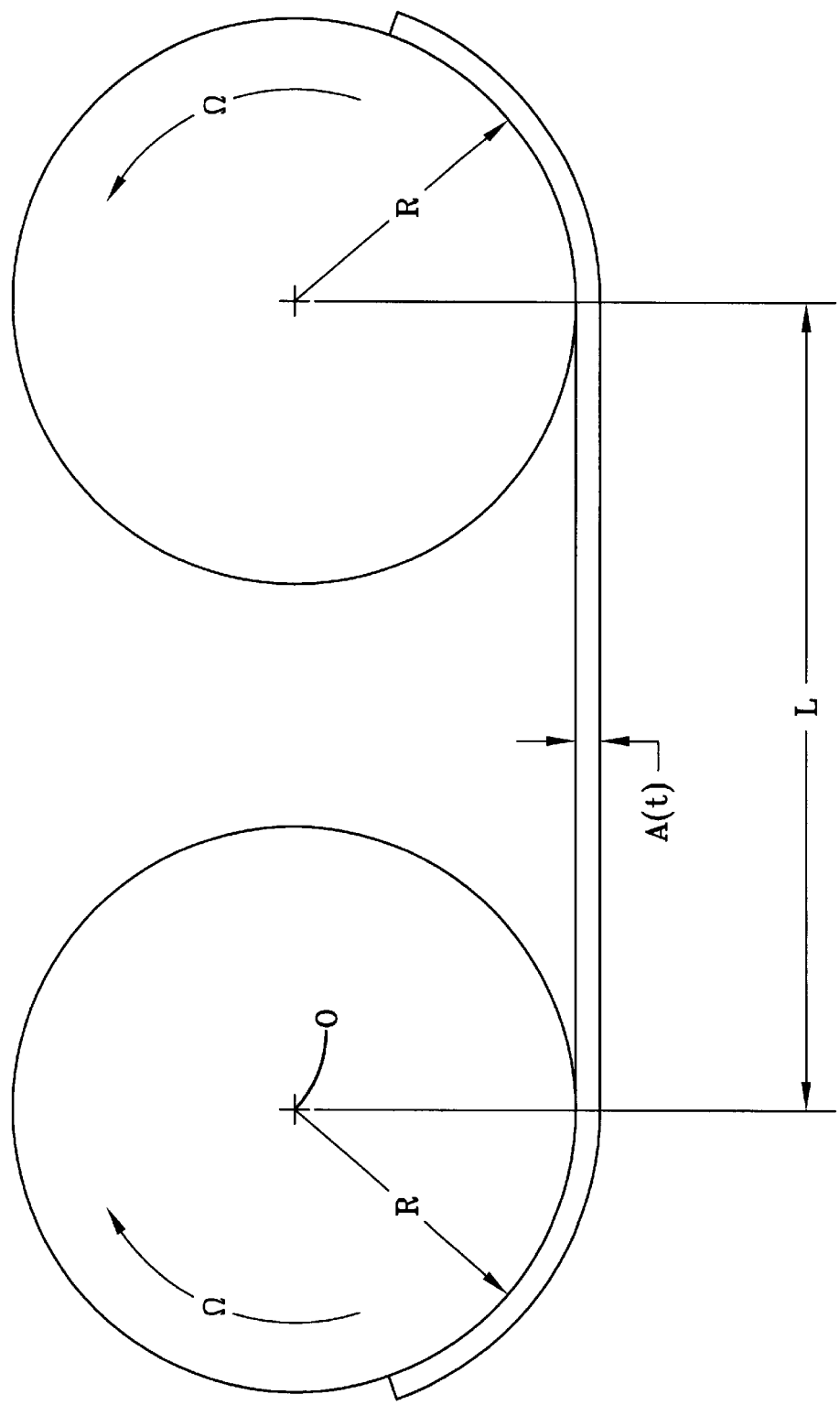
FIG. 7 is a graphic illustration of the top view of the primary and secondary drums as a sample is stretched.

Since both spur gears 18 and 28 are similar, motion of the primary drum 12 drives an equal but opposite rotation of the secondary drum 22. The secondary drum 22 is affixed with precision bearings 26a, 26b to the frame support 24. The constant rotational speed ($\Omega$) of the windup drums 12 and 22 of equal radius (R) imparts a constant, uniform extensional true strain rate, or Hencky strain rate ($\in$) to the unsupported length (L) of the sample 50 such that:

$$\in = 2\Omega R/L$$

as illustrated graphically in FIG. 7.

The extension of the sample 50 offers a resistance to deformation due to the extensional viscosity $\eta_E$ (t) of the material, which in turn offers a resistance to the drum rotation in the form of torque $T_E$. The extensional viscosity of the material can be expressed in the following relationship:

$$\eta_E(t) = \sigma_E(t)/\in = F_E(t)/A(t)/\in$$

where $\sigma_E$ (t) is the instantaneous extensional stress in the unsupported sample, $F_E$ (t) is the instantaneous force required to stretch the unsupported sample, and A(t) is the instantaneous cross-sectional area of unsupported sample. The resultant torque acting on the drums 12 and 22 may then be expressed as:

$$T_E(t) = F_E(t) 2R$$

Both of these expressions may be combined to yield:

$$\eta_E(t) = T_E(t)/(2R\in A(t))$$

By measuring either the resultant torque on the drive drum or the load monitored by the sensing device 34, the extensional viscosity of the material sample may be calculated for a given extensional deformation rate and temperature.

$T_E$ can be resolved by a summation of torques about the axis of rotation of the primary windup drum, point 0 from FIG. 7. During stretch, the resistance of the sample to extend imparts a torque on the gear teeth which in turn imparts a resultant torque, $T_R$, on the system that is borne by the frame support 24, the support member 36, and the load sensing device 34 assembly. Since the bearings 26a, 26b and intermeshing gears 18, 28 also offer resistance to 30 rotation, a summation of torques yields:

$$\Sigma T_0 = 0 = T_R - T_E - T_{Gears} - T_{Bearings} = T_R - T_E - T_{Friction}$$

Thus, the above expression for $\eta_E(t)$ can be rewritten as:

$$\eta_E(t) = (T_R(t) - T_{Friction})/(2R \in A(t))$$

where $T_R(t)$ is the instantaneous resultant torque on the system, and $T_{Friction}$ is the torque losses from the bearings and gears which can be determined from calibration. The instantaneous resultant torque, $T_R(t)$, may then be resolved by monitoring the instantaneous torque on the primary windup drum motor 16 or by monitoring the instantaneous force on the load sensing device 34 and multiplying by the appropriate moment arm, L, about the axis of rotation of the primary windup drum, point 0, as illustrated in FIG. 7.

Now for a sample in simple extension, A(t) can be expressed as:

$$A(t) = A_O \exp(-\in)$$

where $A_O$ is the original cross-sectional area prior to sample extension, and E is the true strain in simple extension. For a constant true strain rate of deformation in simple extension, A(t) can be rewritten as:

$$A(t) = A_O \exp(-\in t)$$

where $\in$ is the constant true strain rate of deformation in simple extension. Substituting the initial expression for $\in$, A(t) can be rewritten as:

$$A(t) = A_O \exp(-2\Omega R\, t/L)$$

Since $\Omega = d(\theta(t))/dt$ where $\theta(t)$ is the angular rotation of the primary windup drum 12 as a function of time, then for a constant rotational drum speed, $\Omega$ may be expressed as:

$$\Omega = (\theta_2 - \theta_1)/(t_2 - t_1)$$

If it is assumed that $\theta_1 = 0$ at $t_1 = 0$ and that a constant rotational speed is achieved instantaneously then the expression for $\Omega$ simplifies to:

$$\Omega = \theta_{2/t2} = \theta(t)/t$$

Assuming no-slip of the fiber on the drum, the above expression can be substituted into the expression for A(t) and the following can be obtained:

$$A(t) = A_O \exp(-2\theta(t)R/L)$$

Thus, the resulting expression for the instantaneous cross-sectional area of a sample is only a function of the angular rotation of the primary windup drum at a given time, t. Beyond the realm of validity of the aforementioned assumptions, however, more rigorous empirical methods for determining instantaneous fiber cross-sectional area should be applied and are well known to those skilled in the art.

Note that each windup drum 12 and 22 can be threaded to allow for fiber alignment and multiple drum rotations to allow for very large true strains as described in Ser. No. WO00/28321. In doing so, however, the increased extensional deformation per drum revolution must be accounted for in the expression for extensional deformation rate, $\in$. In addition, a non-circumferential force component must be accounted for in the torque measurement, $T_R(t)$.

While the invention has been specifically illustrated and described, those skilled in the art will recognize that the invention may be variously modified and practiced without departing from the concepts of the invention. The scope of the invention is limited only by the following claims.

What is claimed is:

1. An extensional rheometer apparatus for measuring the extensional flow response of samples of a material comprising:
   a primary windup drum mounted to a power drive device for rotating the primary windup drum;
   a secondary windup drum rotatably mounted in proximity to the primary windup drum;
   means interconnecting the primary windup drum to the secondary windup drum whereby rotation of the primary windup drum by the power drive device causes the rotation of the secondary windup drum such that the primary and secondary windup drums are counter rotating; and
   a load sensing device for measuring the response of the extensional flow of a low modulus solid sample secured to the primary windup drum and the secondary windup drum.

2. The apparatus of claim 1 wherein the primary and secondary windup drums are in substantially parallel alignment.

3. The apparatus of claim 1 wherein the means for interconnecting the primary and secondary windup drums are first and second gears individually attached to the primary and secondary windup drums and intermeshed such that the primary and secondary windup drums are counter rotating.

4. The apparatus of claim 3 wherein the first and second gears of the primary and secondary windup drums are intermeshed such that the primary and secondary windup drums rotate at the same speed.

5. The apparatus of claim 1 wherein the load sensing device is attached to a support frame for supporting the secondary windup drum.

6. The apparatus of claim 5 wherein outer ends of the secondary windup drum have bearings to provide low frictional rotation between the secondary windup drum and the support frame.

7. An extensional rheometer apparatus for measuring the extensional flow response of samples of a material comprising:
   a primary windup drum mounted to a power drive device for rotating the primary windup drum;
   a plurality of secondary windup drums rotatably mounted in proximity to the primary windup drum;
   means interconnecting the primary windup drum to the plurality of secondary windup drums whereby rotation of the primary windup drum by the power drive device causes the rotation of the secondary windup drums such that the primary and secondary windup drums are counter rotating; and
   a load sensing device attached to each of the secondary windup drums for supporting each of the secondary windup drums and measuring the response to the extensional flow of low modulus solid samples secured to the primary windup drum and each of the plurality of secondary windup drums.

8. The apparatus of claim 7 wherein the primary and plurality of secondary windup drums are in substantially parallel alignment.

9. The apparatus of claim 7 wherein the means for interconnecting the primary and plurality of secondary windup drums are first and second gears individually attached to the primary and plurality of secondary windup drums and intermeshed such that the primary and plurality of secondary windup drums are counter rotating.

10. The apparatus of claim 9 wherein the first and second gears of the primary and plurality of secondary windup drums are intermeshed such that the primary and plurality of secondary windup drums rotate at the same speed.

11. An extensional rheometer apparatus for measuring the extensional flow response of samples of material comprising:

a primary windup drum mounted to a primary power drive device for rotating the primary windup drum;

a secondary windup drum rotatably mounted to a secondary power drive device for rotating the secondary windup drum in proximity to the primary windup drum; and a load sensing device attached to the secondary power drive device for supporting the secondary windup drum and measuring the extensional flow response of a low modulus solid sample secured to the primary windup drum and the secondary windup drum.

12. The apparatus of claim 11 wherein the load sensing device is secured at one end to a support member and at the other end to the secondary power drive device.

13. An extensional rheometer apparatus for measuring the extensional flow response of samples of a material comprising:

a primary windup drum mounted to a primary power drive device for rotating the primary windup drum;

a plurality of secondary windup drums rotatably mounted to a plurality of secondary power drive devices for individually rotating the secondary windup drums in proximity to the primary windup drum; and a plurality of load sensing devices, each attached to one of the plurality of secondary power drive devices for supporting the plurality of secondary windup drums and measuring the extensional flow response of low modulus solid samples secured to the primary windup drum and each of the secondary windup drums.

14. The apparatus of claim 13 wherein each of the plurality of load sensing devices are secured at one end to a support member and at the other end to one of the plurality of secondary power drive devices.

15. A method for measuring the extensional flow response of a material comprising the steps of:

rotating a primary windup drum with a power drive device;

rotating a secondary windup drum in proximity to the primary windup drum such that the primary and secondary windup drums are counter rotating; and supporting the secondary windup drum and measuring the extensional flow response of a low modulus solid sample secured to the primary windup drum and the secondary windup drum with a load sensing device.

16. The method of claim 15 further including the steps of:

rotating a plurality of secondary windup drums in proximity to the primary windup drum; and supporting the plurality of secondary windup drums and measuring the extensional flow response of a plurality of low modulus solid samples secured to the primary windup drum and the plurality of secondary windup drums with a plurality of load sensing devices each attached to the plurality of secondary windup drums.

* * * * *